United States Patent
Christopher

(10) Patent No.: US 6,378,523 B1
(45) Date of Patent: Apr. 30, 2002

(54) ENDOTRACHEAL TUBE HAVING A BEVELED TIP AND ORIENTATION INDICATOR

(75) Inventor: Kent L. Christopher, Denver, CO (US)

(73) Assignee: Evergreen Medical Incorporated, Denver, CO (US)

( * ) Notice: Subject to any disclaimer, the term of this patent is extended or adjusted under 35 U.S.C. 154(b) by 0 days.

(21) Appl. No.: 09/525,490

(22) Filed: Mar. 15, 2000

(51) Int. Cl.$^7$ .............................................. A61M 16/00
(52) U.S. Cl. ............................. 128/207.14; 128/200.26
(58) Field of Search ........................ 128/207.14, 207.15, 128/207.18, 200.26, 912, DIG. 26; 116/280, 307, 308, 311–315, 318, 319

(56) References Cited

U.S. PATENT DOCUMENTS

| | | | |
|---|---|---|---|
| 4,027,659 A | * 6/1977 | Slingluff ........................ 128/2 |
| 4,050,466 A | 9/1977 | Koerbacher | |
| 4,105,732 A | * 8/1978 | Slingluff ..................... 264/104 |
| 4,419,095 A | 12/1983 | Nebergall et al. | |
| 4,469,483 A | 9/1984 | Becker et al. | |
| 4,588,399 A | 5/1986 | Nebergall et al. | |
| 4,898,168 A | * 2/1990 | Yule ...................... 128/207.15 |
| 5,017,193 A | * 5/1991 | Fields ......................... 604/270 |
| 5,045,071 A | * 9/1991 | McCormick et al. ....... 604/280 |
| 5,052,386 A | * 10/1991 | Fischer, Jr. ............ 128/207.15 |
| 5,078,701 A | * 1/1992 | Grassi et al. ................ 604/264 |
| 5,259,371 A | * 11/1993 | Tonrey ................... 128/200.26 |
| 5,318,530 A | * 6/1994 | Nelson, Jr. ..................... 604/96 |
| 5,353,787 A | * 10/1994 | Price ....................... 128/200.26 |
| 5,515,844 A | * 5/1996 | Christopher ........... 128/207.14 |
| 5,623,924 A | * 4/1997 | Lindenman et al. ... 128/207.17 |
| 5,694,929 A | * 12/1997 | Christopher ........... 128/207.14 |
| 5,873,362 A | 2/1999 | Parker | |
| 6,053,166 A | * 4/2000 | Gomez ................... 128/200.26 |

\* cited by examiner

Primary Examiner—John G. Weiss
Assistant Examiner—Teena Mitchell
(74) Attorney, Agent, or Firm—Dorr, Carson, Sloan & Birney, P.C.

(57) ABSTRACT

A method and apparatus for intubation of a patient's airway uses an endotracheal tube having a beveled distal end with a tip on the posterior wall of the endotracheal tube, and a visual indicator extending along the endotracheal tube. For example, the visual indicator can be a radio-opaque stripe extending the length of the anterior and/or posterior wall of the endotracheal tube. To use the apparatus with the patient in a supine position, the healthcare provider first takes a position above the patient's head. The distal end of the endotracheal tube is then inserted into the patient's mouth so that the visual indicator remains visible to the healthcare provider when viewed from above. The healthcare provider advances the endotracheal tube into the patient's airway while monitoring the position of the visual indicator to ensure that the tip at the distal end of the endotracheal tube passes through the midline of the wider posterior portion of the opening in the patient's larynx.

17 Claims, 2 Drawing Sheets

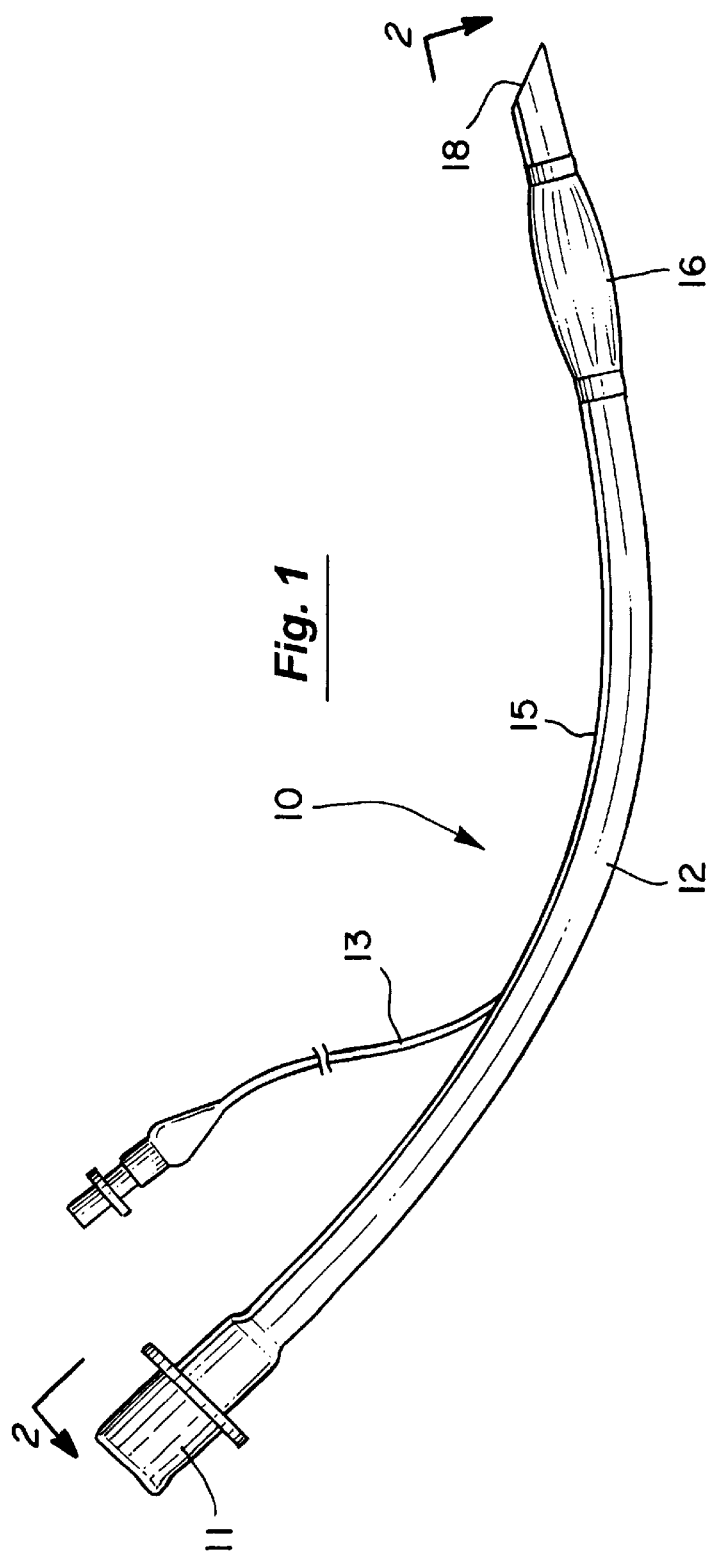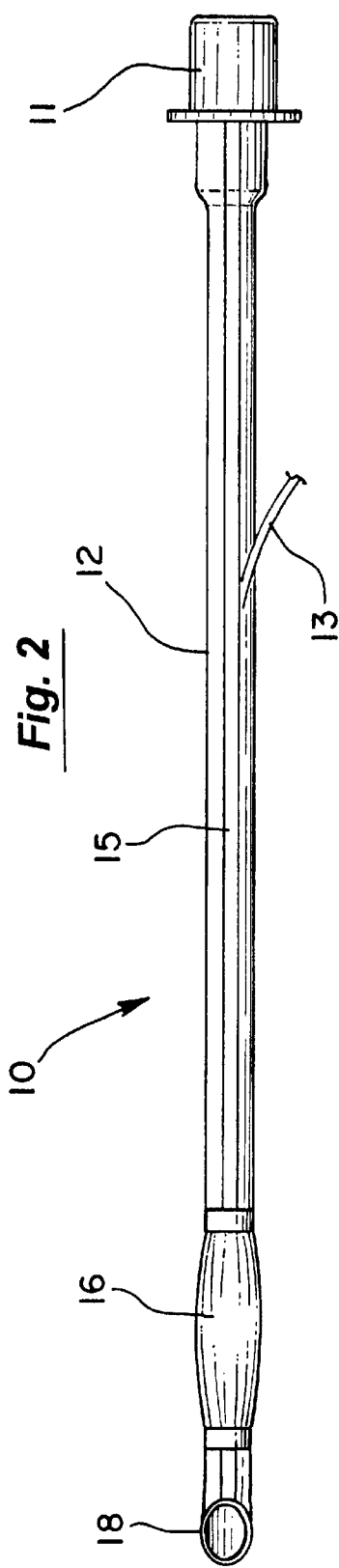

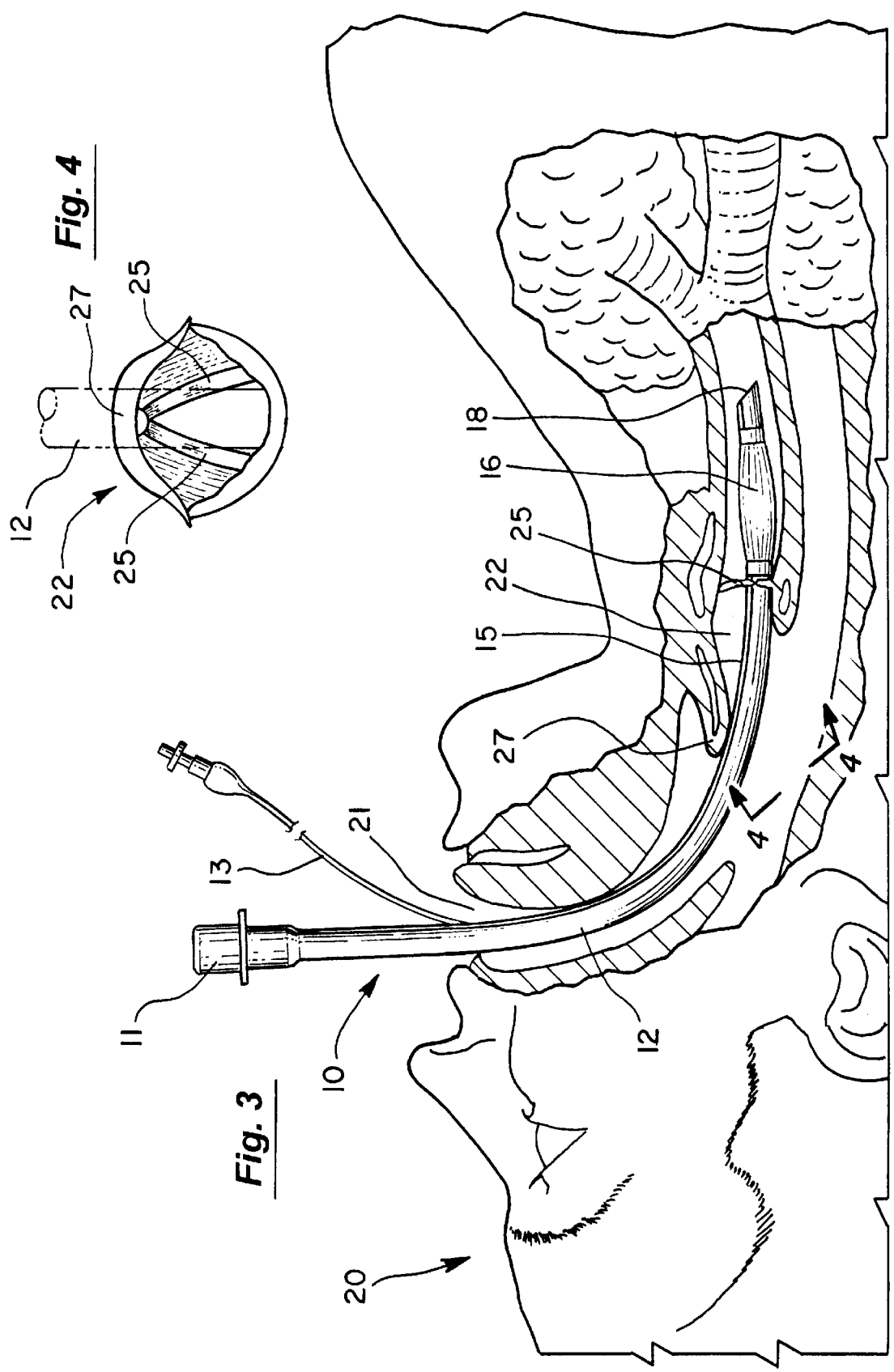

ENDOTRACHEAL TUBE HAVING A BEVELED TIP AND ORIENTATION INDICATOR

BACKGROUND OF THE INVENTION

1. Field of the Invention.

The present invention relates generally to the field of endotracheal tubes. More specifically, the present invention discloses an endotracheal tube having a beveled tip on its posterior wall and a radio-opaque stripe or other visual indicator to show proper orientation of the endotracheal tube as it is inserted into a patient's airway.

2. Statement of the Problem.

Endotracheal tubes have been used for many years for ventilating patients. An endotracheal tube is typically a length of flexible tube with a connector at its proximal end for attachment to a ventilator, and an inflatable cuff adjacent to its distal end. The endotracheal tube is inserted through the patient's mouth and advanced along the patient's airway until the distal end of the endotracheal tube passes through the patient's larynx. The cuff is then inflated through a small secondary lumen to occlude the airway surrounding the endotracheal tube, so that the patient's ventilation is completely regulated and supplied by the ventilator.

Conventional endotracheal tubes are available in a variety of configurations. Some endotracheal tubes have a flexible plastic tube that can bend to accommodate a range of variations in patient anatomy. The opening between the patient's vocal cords is a constriction in the airway that can be difficult for the healthcare provider to navigate with an endotracheal tube. The larynx is also a relatively delicate structure that can be easily bruised or torn. Ideally, the healthcare provider should be able to advance the distal end of the endotracheal tube through the opening between the patient's vocal cords without causing trauma to the larynx or other portions of the patient's airway.

In an effort to address these problems, some commercially available endotracheal tubes are equipped with a beveled distal tip. However, they are generally inserted at a random rotational orientation by healthcare providers. For example, in the case of a flexible endotracheal tube, many healthcare providers spin the endotracheal tube about its longitudinal axis while advancing it into the patient's airway. These types of endotracheal tubes do not inherently have anterior or posterior sides. The spinning motion of the beveled tip tends to center the distal end of the endotracheal tube as it passes through the larynx and therefore may require less forward force to advance the endotracheal tube, but does little to prevent damage to the larynx caused by the rotating distal tip.

Other conventional endotracheal tubes are somewhat flexible, but have a preformed curvature that dictates a specific orientation for insertion of the endotracheal tube into the patient's airway. These endotracheal tubes typically have a distal end that is beveled from the side, with a tip formed on the right side of the tube to minimize obstruction to the healthcare provider's view of the larynx during insertion of the endotracheal tube (see, U.S. Pat. No. 5,873,362, col. 1, lines 20–34).

Some endotracheal tubes are also equipped with a radio-opaque stripe or a radio-opaque distal tip for monitoring the depth of insertion into the airway by means of x-ray or fluoroscopic imaging. However, these radio-opaque indicators are not normally used in monitoring the rotational orientation of the endotracheal tube.

Therefore, a need exists for an endotracheal tube having a distal tip that can be readily oriented by the healthcare provider to minimize the risk of trauma to the patient's larynx. In particular, contrary to the conventional wisdom, placing the distal tip of the endotracheal tube on the posterior surface of the endotracheal tube helps to guide the endotracheal tube through the wider posterior opening between the patient's vocal cords with a minimum resistance and trauma.

3. Prior Art.

The prior patents in the field includes the following:

| Inventor | Patent No. | Issue Date |
|---|---|---|
| Parker | 5,873,362 | Feb. 23, 1999 |
| Nebergall et al. | 4,588,399 | May 13, 1986 |
| Becker et al. | 4,469,483 | Sept. 4, 1984 |
| Nebergall et al. | 4,419,095 | Dec. 6, 1983 |
| Koerbacher | 4,050,466 | Sep. 27, 1977 |
| Slingluff | 4,027,659 | June 7, 1977 |

Parker discloses an endotracheal tube having a beveled distal tip. The bevel extends toward, but not completely through the anterior wall of the tube, thus leaving a curved lip projecting from the anterior wall of the endotracheal tube. However, this anterior tip must pass through the narrower, anterior portion of the opening between the patient's vocal cords, which may increase the risk of trauma. The rearward bevel and curved lip would also tend to accumulate mucus. If a fiber optic scope is used to insert the tube, the curved tip would at least partially block the view from within the lumen. If a fiber optic scope is used as a guide and the endotracheal tube is then advanced over the fiber optic scope, the curved tip at the distal end of the endotracheal tube would tend to move the endotracheal tube off-center relative to the fiber optic scope. Since healthcare providers are generally trained to the keep the fiber optic scope centered within the patients airway, this would tend to result in the endotracheal tube being advanced off-center through the opening in the vocal cords, which increases the risk of trauma to the vocal cords. In addition, if a suction catheter is advanced into the endotracheal tube, the rearward bevel at the distal end of the endotracheal tube would also tend to push the suction catheter into the mucosa lining the posterior surface of the airway, thereby further increasing the risk of trauma.

The patents to Nebergall et al. show a cannula with a radio-opaque tip. In particular, FIG. 1 of these patents shows an endotracheal tube with a beveled radio-opaque tip for monitoring the orientation of the tip in x-ray or fluoroscopic images.

Slingluff and Becker et al. disclose examples of several types of medical tubes or catheters with radio-opaque stripes.

Koerbacher discloses an endotracheal tube with a beveled distal end and a tip on the anterior wall of the tube. The distal tubular portion is connected by a flexible accordion section to the proximal tubular portion of the endotracheal tube.

4. Solution to the Problem.

None of the prior art references discussed above show an endotracheal tube with a beveled distal tip on the posterior wall of the endotracheal tube, and a visual indicator (e.g., a radio-opaque stripe) on the wall of the endotracheal tube indicating the rotational orientation of the endotracheal tube. This configuration allows the healthcare provider to continually monitor the rotational position of the endotracheal tube so that its distal tip passes through the wider posterior portion of the opening in the patient's larynx, thereby reducing the force necessary to advance the endotracheal tube and minimizing the risk of trauma to the patient's larynx. The visual indicator on the proximal end of the endotracheal tube remains within the normal visual field of the healthcare provider throughout the procedure and can be continually monitored to maintain the proper rotational orientation for the endotracheal tube.

SUMMARY OF THE INVENTION

This invention provides a method and apparatus for intubating a patient's airway using an endotracheal tube having a beveled distal end with a tip on the posterior wall of the endotracheal tube, and a visual indicator extending along the wall of the endotracheal tube. For example, the visual indicator can be a radio-opaque stripe extending the length of the anterior and/or posterior wall of the endotracheal tube. To use the apparatus with the patient in a supine position, the healthcare provider first takes a position above the patient head. The distal end of the endotracheal tube is then inserted into the patient's mouth so that the visual indicator remains visible to the healthcare provider when viewed from above. The healthcare provider advances the endotracheal tube into the patient's airway while monitoring the position of the visual indicator to ensure that the tip at the distal end of the endotracheal tube passes through the midline of wider posterior portion of the opening in the patient's larynx.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 1 is a side elevational view of an endotracheal tube 10 embodying the present invention.

FIG. 2 is a front view of the endotracheal tube 10 corresponding to FIG. 1, showing the radio-opaque stripe 15.

FIG. 3 is a cross-sectional view of the mouth 21 and airway 22 of the patient 20 after the distal end of the endotracheal tube 12 has been advanced to a position below the larynx 25.

FIG. 4 is a detail cross-sectional view of the patient's airway 22 taken along lines 4—4 in FIG. 3, illustrating insertion of the endotracheal tube 12 through the space between the patient's vocal cords 25.

DETAILED DESCRIPTION OF THE INVENTION

Structure of the Endotracheal Tube

Turning to FIG. 1, a side elevational view is provided of an endotracheal tube 10 embodying the present invention. FIG. 2 is a corresponding front view of the endotracheal tube 10. As shown in these figures, the endotracheal tube 10 includes a tubular member 12 with a connector 11 at its proximal end suitable for removable attachment to an external ventilator that will be used to ventilate the patient.

The tubular member 12 could be a silicone rubber tube embedded with a helical wire reinforcement. However, other polymer or other rubber-based materials could be readily substituted. The tubular member 12 should be sufficiently flexible to follow the contour of the patient's airway 22 without requiring excessive force and to accommodate variations in patient size and anatomy. However, the tubular member 12 must have sufficient rigidity to be advanced into the patient's airway 22 without buckling. Optionally, the tubular member 12 can be preformed with a curve approximating the contour of the patient's airway 22.

The distal tip 18 of the tubular member 12 is beveled to form a tip on the posterior wall of the endotracheal tube 10, as illustrated in FIG. 1. Preferably, the distal tip 18 is centered on the midline of the posterior wall of the endotracheal tube 10. The distal tip 18 should be made of a material that is soft enough to be atraumatic.

An inflatable cuff 16 is attached to the exterior surface of the tubular member 12 near its distal end, so that the airway surrounding the endotracheal tube 10 can be occluded at the time the patient is connected to a ventilator, thereby allowing the ventilator to completely regulate the patient's respiration. Inflation and deflation of the cuff 16 is controlled through a small secondary lumen 13 attached to the exterior of the tubular member 12.

A visual indicator 15 is placed on the wall of the endotracheal tube 10 to indicate the rotational orientation of the distal tip 18 of the tubular member 12 for the healthcare provider. For example, the visual indicator 15 can be a radio-opaque stripe extending along the anterior wall of the tubular member 12 from its proximal end to its distal end, as depicted in FIG. 2. This embodiment allows the stripe to serve the dual purposes of providing a visual indicator for the rotational orientation of the distal tip, and showing the position of the distal tip 18 of the endotracheal tube 10 relative to the patient's airway 22 and larynx 25 on x-ray or fluoroscopic images. Alternatively, the visual indicator 15 can be placed on the proximal portion of the tubular member 12 that remains visible to the healthcare provider after the endotracheal tube 10 has been inserted.

The present invention can be equipped with a plurality of visual indicators to help ensure that the healthcare provider can monitor the orientation of the endotracheal tube from virtually any point of view. For example, the tubular member 12 can be provided with a stripe in a contrasting color extending along its posterior wall in addition a visual indicator on its anterior wall. The posterior visual indicator can be a white, radio-opaque stripe (e.g., barium sulfate) to assist in viewing the position of the distal tip on the posterior wall in x-ray images, while the anterior visual indicator is a bright, contrasting color. The tubular member 12 can also be made of a clear or translucent material to enable the healthcare provider to view the visual indicator(s) through the endotracheal tube 10.

Method of Use

To use the endotracheal tube 10, the healthcare provider first takes a position relative to the supine patient above the patient's mouth 21. The healthcare provider bends forward over the patient's head so that the healthcare provider can look directly downward at the patient. This is consistent with the usual position taken by a healthcare provider during endotracheal intubation. The distal end 18 of the endotracheal tube 10 is then inserted into the patient's mouth 21 so that the visual indicator 15 remains visible to the healthcare provider while looking downward at the patient's head. If a conventional guide blade is used to facilitate insertion, the endotracheal tube 10 is typically inserted at a slight angle toward the top of the patient's head, so that the anterior side of the endotracheal tube 10 faces upward to some degree.

The healthcare provider advances the endotracheal tube 10 past the epiglottis 27 and into the patient's airway 22 while monitoring the position of the visual indicator 15 to ensure that the distal tip 18 of the endotracheal tube 10 passes through the posterior portion of the opening in the patient's larynx 25. In other words, the healthcare provider maintains the endotracheal tube 10 in a rotational orientation such that the visual indicator continues to point down the midline of the patient toward the healthcare provider. Thus, the visual indicator 15 should remain in the middle of the field of view of the healthcare provider and can be easily observed throughout the insertion process. FIG. 3 is a cross-sectional view of the mouth 21 and airway 22 of the patient 20 after the distal end of the endotracheal tube 10 has been advanced to a position below the larynx 25 and above the patient's carina.

During this insertion process, the distal tip 18 slides easily along the posterior wall of the patient's airway and helps to maintain proper curvature of the endotracheal tube 10 so that it can advance along the airway 22. When the distal tip 18 of the endotracheal tube 10 reaches the patient's larynx 25, the tip 18 initially tends to follow the opening between the vocal cords on the posterior side of the larynx 25. Thus, the distal tip 18 of the endotracheal tube 10 tends to center itself between the vocal cords, which also brings the entire distal portion of the endotracheal tube 10 into proper lateral alignment with the larynx 25. The space between the vocal cords 25 narrows from the posterior to the anterior portion of the larynx, providing a somewhat wedge-shaped opening between the vocal cords 25. The beveled edge of the distal tip 18 of the endotracheal tube 10 also tends to follow this wedge-shaped opening between the vocal cords 25, and thereby guiding the entire distal portion of the endotracheal tube through the wider posterior portion of the opening between the vocal cords 25. FIG. 4 is a detail cross-sectional view of the patient's airway 22 taken along lines 4—4 in FIG. 3, illustrating insertion of the endotracheal tube 12 through the opening between the patient's vocal cords 25.

Following insertion of the endotracheal tube 10, the cuff 16 at the distal end of the endotracheal tube 10 is inflated via the secondary lumen 13 to occlude the patient's airway 22 surrounding the endotracheal tube 10. A ventilator is then attached to the connector 11 at the proximal end of the endotracheal tube 10 to provide air/oxygen for the patient.

Alternatively, a fiber optic laryngoscope can be used to guide insertion of the endotracheal tube 10 into the patient's airway. With the patient in a supine position, the healthcare provider typically takes a position above the patient' head to operate the laryngoscope and a visual indicator on the posterior wall of the endotracheal tube 10 would be more readily visible. However, an anterior visual indicator would also remain visible if the tubular member 12 of the endotracheal tube is clear or translucent. With this method of insertion, the fiber optic scope is initially inserted along the patient's airway and visually navigated through the midline of the opening in the vocal cords 25. The endotracheal tube 10 is then inserted over the fiber optic probe. The beveled distal tip 18 of the endotracheal tube 10 helps to keep the endotracheal tube 10 centered with respect to the fiber optic probe as it advances so that the endotracheal tube 10 passes through the midline of the opening of the vocal cords 25.

Finally, the endotracheal tube can be inserted from the position above the patient's head via the nasopharyngeal airway. Here again, a posterior visual indicator would be more visible, although an anterior visual indicator could be used if the tubular member 12 is clear or translucent.

The above disclosure sets forth a number of embodiments of the present invention. Other arrangements or embodiments, not precisely set forth, could be practiced under the teachings of the present invention and as set forth in the following claims.

I claim:

1. An endotracheal tube for insertion into a patient's upper airway, through the larynx, and into the trachea, said endotracheal tube comprising:

a tubular member extending between a proximal end and a distal end having a posterior wall intended for insertion adjacent to the posterior portion of a patient's trachea;

a beveled distal end on said tubular member forming a tip on said posterior wall of said tubular member, whereby the tip on the distal end of the tubular member passes through the posterior portion of the opening in a patient's larynx as the endotracheal tube is advanced into a patient's trachea; and a visual indicator on said tubular member indicating the rotational orientation of said tip of said tubular member during insertion of the endotracheal tube along a patient's airway.

2. The endotracheal tube of claim 1 wherein said visual indicator comprises a stripe extending along the anterior wall of said tubular member.

3. The endotracheal tube of claim 2 wherein said stripe is substantially radio-opaque.

4. The endotracheal tube of claim 1 wherein said visual indicator comprises a stripe extending along the posterior wall of said tubular member.

5. The endotracheal tube of claim 1 wherein said tubular member comprises a silicone rubber tube.

6. The endotracheal tube of claim 5 wherein said tubular member further comprises a reinforcing wire embedded in said silicone rubber tube.

7. The endotracheal tube of claim 1 wherein said tubular member comprises a flexible tube.

8. An endotracheal tube for insertion into a patient's upper airway, through the larynx, and into the trachea, said endotracheal tube comprising:

a tubular member extending between a proximal end and a distal end having a posterior wall intended for insertion adjacent to the posterior portion of a patient's trachea, and an opposing anterior wall;

a beveled distal end on said tubular member forming a tip on said posterior wall of said tubular member, whereby the tip on the distal end of the tubular member passes through the posterior portion of the opening in a patient's larynx as the endotracheal tube is advanced into a patient's trachea; and a visible stripe extending from said proximal end to said distal end of said tubular member indicating the rotational orientation of said tip of said tubular member during insertion of the endotracheal tube along a patient's airway.

9. The endotracheal tube of claim 8 wherein said stripe is substantially radio-opaque.

10. The endotracheal tube of claim 8 wherein said tubular member comprises a silicone rubber tube.

11. The endotracheal tube of claim 10 wherein said tubular member further comprises a reinforcing wire embedded in said silicone rubber tube.

12. The endotracheal tube of claim 8 wherein said tubular member comprises a flexible tube.

13. The endotracheal tube of claim 8 wherein said stripe extends along the anterior wall of said tubular member.

14. The endotracheal tube of claim 8 wherein said stripe extends along the posterior wall of said tubular member.

15. A method for intubating of a patient's airway using an endotracheal tube having a beveled distal end with a tip on the posterior wall of the endotracheal tube, and a visual indicator extending along the endotracheal tube, said method comprising:

taking a position relative to the patient above the patient's mouth;

inserting the distal end of the endotracheal tube into the patient's mouth so that the visual indicator remains visible; and advancing the endotracheal tube into the patient's airway while monitoring the position of the visual indicator to ensure that the tip at the distal end of the endotracheal tube passes through the posterior portion of the opening in the patient's larynx.

16. The method of claim 15 wherein the position of the visual indicator is monitored by observing the orientation of the visual indicator at the proximal end of the endotracheal tube.

17. The method of claim 15 wherein visual indicator is substantially radio-opaque, and wherein the position of the visual indicator is monitored by x-ray images of the distal end of the endotracheal tube.

* * * * *